US006852485B1

(12) United States Patent
Meyer

(10) Patent No.: US 6,852,485 B1
(45) Date of Patent: Feb. 8, 2005

(54) METHOD FOR IDENTIFYING A COMPOUND FOR THE TREATMENT OF MICROORGANISM INFECTIONS BY INHIBITING ENERGY STORAGE AND UTILIZATION IN PATHOGENS

(75) Inventor: Christopher Meyer, Fullerton, CA (US)

(73) Assignee: California State University Fullerton Foundation, Fullerton, CA (US)

( * ) Notice: Subject to any disclaimer, the term of this patent is extended or adjusted under 35 U.S.C. 154(b) by 0 days.

(21) Appl. No.: 10/055,749

(22) Filed: Jan. 22, 2002

(51) Int. Cl.[7] .......................... C12Q 1/00; C12Q 1/48; C12Q 1/02; C12Q 1/18
(52) U.S. Cl. ................. 435/4; 435/14; 435/15; 435/29; 435/32
(58) Field of Search ................. 435/15, 14, 4, 435/29, 32

(56) References Cited

U.S. PATENT DOCUMENTS

| | | |
|---|---|---|
| 4,190,495 A | 2/1980 | Curtiss, III |
| 5,349,123 A | 9/1994 | Shewmaker et al. |
| 5,461,143 A | 10/1995 | Wong et al. |
| 5,593,887 A | 1/1997 | Wong et al. |
| 5,684,144 A | 11/1997 | Romeo |
| 5,753,483 A | 5/1998 | Elbein |
| 5,759,823 A | 6/1998 | Wong et al. |
| 5,770,407 A | 6/1998 | Wong et al. |
| 5,824,790 A | 10/1998 | Keeling et al. |
| 5,871,951 A | 2/1999 | Weiser |
| 5,928,932 A | 7/1999 | Jarvis et al. |
| 5,969,214 A | 10/1999 | Stalker et al. |
| 6,057,493 A | 5/2000 | Willmitzer et al. |
| 6,143,539 A | 11/2000 | Kiy et al. |
| 6,168,934 B1 | 1/2001 | Wong et al. |
| 6,268,471 B1 * | 7/2001 | Romeo ................. 530/324 |

OTHER PUBLICATIONS

Dietzler et al., "Identification of GTP as a Physiologically Relevant Inhibitor of *Escherica coli* ADP–Glucose Synthetase", BBRC 122 (1) : 289–296 (1984).*
Miller, Jeffrey H., "Experiments in molecular genetics," Cold Spring Harbor Laboratory 1972, pp. 31–34.
Lin, Jinlai et al., "Synthesis of a boron analogue . . . ," Tetrahedron Letters 41, 2000, pp. 6701–6704.
Inglesias, Alberto A. et al., "Bacterial glycogen and plant starch biosynthesis," Biochemical Education 20 (4), 1992, pp. 196–203.
Preiss, Jack "ADPglucose pyrophoshorylase: basic science and applications in biotechnology," pp. 259–279.
NCBI Accession No. CAB89282, GI: 7671532, Apr. 29, 2000.
NCBI Accesion No. 008326, GI:2811060, May 30, 2000.
NCBI Accession No. P39669, GI:729581, Dec. 15, 1998.
NCBI Accession No. AAK02627, GI:1270807, Mar. 08, 2001.
Abstract—Sharma et al., "Structure of isocitrate lyase, a persistence factor of Mycobacterium tuberculosis" vol. 7, No. 8, Aug. 2000, pp. 663–668.
Punt, Jenni "Carbohydrate Metabolism", Biochemistry: Molecular Basis of disease, Biology 304th, Mar. 26, 2001, pp. 1–2.

* cited by examiner

*Primary Examiner*—Sandra E. Saucier
(74) *Attorney, Agent, or Firm*—BioTechnology Law Group; Daniel M. Chambers

(57) ABSTRACT

A method and pharmaceutical composition for inhibiting infections of pathogenic microorganisms by inhibiting the production of ADP-glucose, particularly by inhibiting the activity of ADP-glucose pyrophosphorylase or glycogen synthase.

7 Claims, 5 Drawing Sheets

METHOD FOR IDENTIFYING A COMPOUND FOR THE TREATMENT OF MICROORGANISM INFECTIONS BY INHIBITING ENERGY STORAGE AND UTILIZATION IN PATHOGENS

FIELD OF THE INVENTION

The present invention is directed to the use of bacterial enzymes as targets for antibiotic therapy and the treatment of microorganism infections, particularly by inhibiting enzymes involved in energy storage and utilization.

BACKGROUND OF THE INVENTION

Starch, a complex polymer of glucose, is present in most green plants in practically every type of tissue and is the major intracellular reserve polysaccharide in photosynthetic organisms. The glucan accumulates during development of storage or seed tissues and is catabolized to serve as a source of energy. In the animal kingdom, as well as in fungi, yeast and bacteria, the primary reserve polysaccharide is glycogen. Glycogen is a polysaccharide containing linear molecules with α-1,4 glucosyl linkages and is branched via α-1,6-glucosyl linkages. Although glycogen is analogous to starch with regard to linkages, glycogen exhibits a different chain length and a different degree of polymerization.

The following common reactions are shared by the biosynthetic pathways of bacterial glycogen and of starch in algae and higher plants:

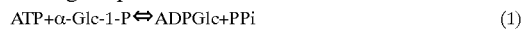  (1)

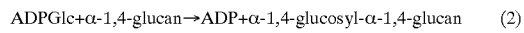  (2)

  (3)

In step (1), ADP Glucose (ADPGlc) is synthesized from ATP and glucose-1-phosphate in the rate-limiting reaction which is catalyzed (in plants and bacteria) by ADP-glucose pyrophosphorylase (also referred to as ADPGlc PPase; or ADPG PPase, or glucose-1-P adenyltransferase, or as enzyme EC. 2.7.7.27). The chain elongation step (2) is catalyzed by glycogen synthase (also referred to a GS, gly A, or as enzyme EC. 2.4.1.21).

1. ADP-glucose phyrophosphorylase
The reaction scheme catalyzed by ADPGlc PPase is shown below:

Significant research has led to cloning and sequencing genes which code for ADP-glucose pyrophosphorylase in plants for the purpose of modulating sucrose and starch content in plants. For example, U.S. Pat. Nos. 5,498,831 and 5,773,693 to Burgess et al. described the sequence of Pea ADP-glucose pyrophosphorylase subunit genes and the use of those genes to transform plant cells in order to provide plants that have increased sucrose content.

U.S. Pat. No. 6,184,438 to Hannah describes mutant genes encoding plant ADP-glucose pyrophosphorylases and the use of those genes to produce transformed plants having enhance germination characteristics but without any diminishment in food quality or flavor.

U.S. Pat. No. 6,057,493 to Willmitzer et al. describes the use of anti-sense DNA sequences encoding ADP-glucose pyrophosphorylase from potato to produce transformed plants with a reduction in starch concentration and an increase in the concentration of at least sucrose.

The genes which code for several bacterial ADPGlc PPases have also been cloned and recombinant enzymes have been prepared. See for example, Preiss, J., and M. N. Sivak, M. N. (1998) *Genet. Eng.* (N.Y.) 20, 177–223; Preiss, J. (1996) In *Escherichia coli* and *Salmonella typhimurium:* Cellular and Molecular Biology (Neidhart, F. C., Ed.), $2^{nd}$ ed., Vol 1 pgs. 10115–1024, ASM Press; Preiss, J., and Romeo, T. (1989) *Advances in Microbial Physiology* 30, 183–238. DNA sequences have also been elucidated for certain bacterial ADP-glucose pyrophosphorylase enzymes. For example, U.S. Pat. No. 5,349,123 to Shewmaker et al. describes a nucleic acid construct which encodes an *E.coli* ADP-glucose pyrophosphorylase and the use of that construct to transform plant cells to modify biosynthesis of a glucan in the plant.

2. Glycogen Synthase

The reaction scheme in bacteria catalyzed by glycogen synthase is shown below:

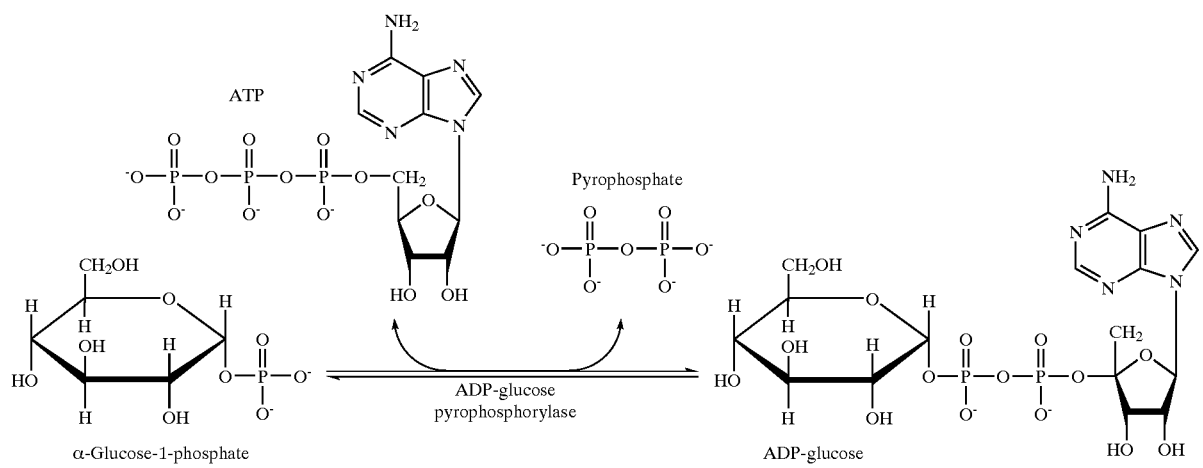

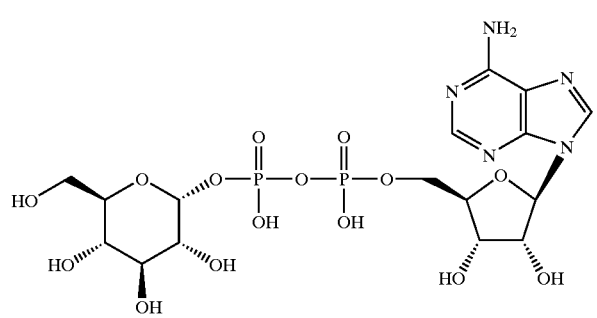

ADP Glucose

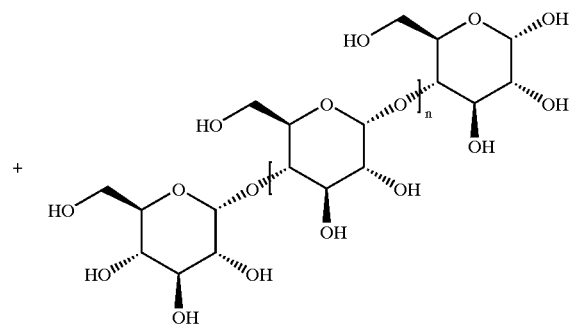

α-1,4-glucan

| glucogen synthase

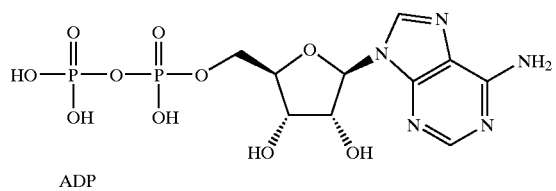

ADP (α-1,4-glucan)$_{n+1}$

The "corresponding" reaction in mammals is similar except that the nucleoside diphosphate sugar substrate is UDP glucose, and the catalyzing enzyme is EC 2.4.1.11.

Genes encoding mammalian glycogen synthases have been cloned and sequenced (See Browner et al., Proc. Nat. Acad. Sci. (1989) 86:1443–1447; Bai et al., J. Biol. Chem. (1990) 265:7843–7848), and the genes encoding bacterial glycogen synthases have also been cloned and sequenced. (See for example U.S. Pat. No. 5,969,214.)

SUMMARY OF THE INVENTION

While previous research has focused on modifying the activity of glycogen synthase or ADP-glucose pyrophosphorylase to modify starch content in plants, the present inventor has determined that, since the catabolism and metabolism of energy storage pathways are critical to viability of bacteria, the inhibition of such pathways in bacteria provides a novel class of antibiotics for the treatment of bacterial infections. Further, numerous studies have indicated that glycogen plays an important role in the survival of the bacterial cell (Strange, R. E. (1968) Nature 220, 606; Strange et al (1961) J. Gen. Microbiol. 25, 61; Van Houte, J., and Jansen, H. M. (1970) J. of Bacteriol. 101, 1083). Whereas current antibiotics are characterized by inhibition of protein synthesis, DNA synthesis and cell wall synthesis, this novel class of antibiotics is characterized by inhibition of energy storage and utilization pathways.

The inventor has particularly noted that production of ADP-glucose is critical to viability of bacteria, and since ADP-glucose pyrophosphorylase is not present in mammals, the enzyme provides an excellent target for inhibition of bacterial growth, thereby providing a means for inhibiting the growth of microorganisms and treating bacterial infections.

Similarly, since the glycogen synthase in many pathogenic bacteria is different than the glycogen synthase in mammals, that enzyme also provides an excellent target for inhibition of bacterial growth and treating bacterial infections.

In one aspect, the present invention is directed to a method for treating a microorganism infection by administering an effective amount of a compound capable of inhibiting the production and/or utilization of ADP-glucose.

It is another aspect of the invention to provide a method for treating a microorganism infection by administering an effective amount of a compound capable of inhibiting the activity of ADP-glucose pyrophosphorylase and/or glycogen synthase.

It is a further aspect of the invention to provide a method of identifying a compound capable of inhibiting the growth of pathogenic microorganisms which comprises identifying a compound which inhibits an enzyme important in the catabolism and metabolism of energy storage pathways, particularly a compound that inhibits the activity of ADP-glucose pyrophosphorylase and/or glycogen synthase.

DETAILED DESCRIPTION OF THE INVENTION

Figure 1:
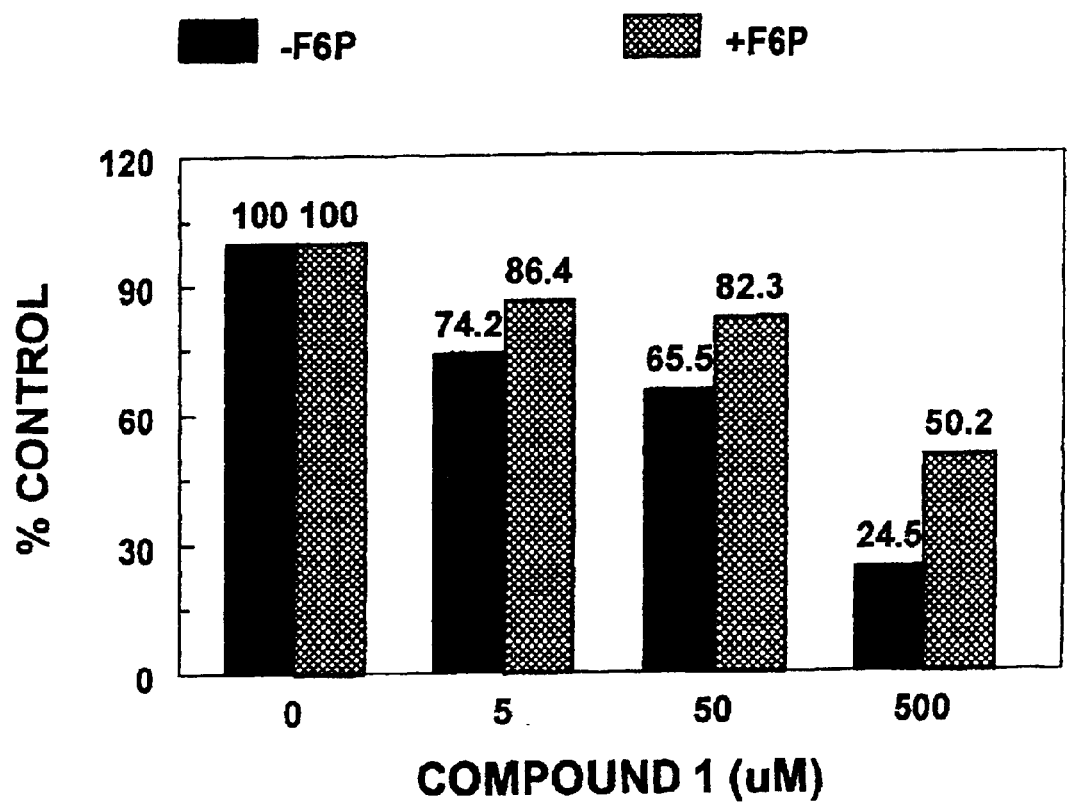
FIGS. 1–5 are graphs plotting the results of experiments testing the inhibiting effect of ADP-glucose borano analogs on an ADP-glucose Ppase enzyme in in vitro enzyme tests.

The present inventor has discovered that while certain important pathogenic microorganisms require the activity of ADP-glucose pyrophosphorylase (EC 2.7.7.27) to produce ADP-glucose, that enzyme is not present in mammals, particularly not in humans. In addition, the present inventor has recognized that the glycogen synthase (EC 2.4.1.21) in many pathogenic bacteria as the ADPGlucose dependent glucan chain lengthening enzyme is not present in mammals, particularly not in humans. As a result, the present inventor has first determined that inhibition of ADP-glucose pyrophosphorylase (EC 2.7.7.27) and/or glycogen synthase (EC 2.4.1.21) provide excellent targets for inhibiting the growth of pathogenic microorganisms, while not inhibiting any important biosynthetic pathway in humans. As noted above, in plants and most bacteria, ADP-glucose pyrophosphorylase catalyzes the reaction of α-glucose-1-phosphate with ATP to produce ADP-glucose. In mammals and in eukaryotic microorganisms, the "corresponding" reaction is catalyzed by UDP-glucose pyrophosphorylase by transferring a glucosyl residue from UDP-glucose, as shown below:

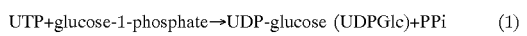

UTP+glucose-1-phosphate→UDP-glucose (UDPGlc)+PPi    (1)

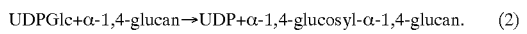

UDPGlc+α-1,4-glucan→UDP+α-1,4-glucosyl-α-1,4-glucan.    (2)

Step (1) in this pathway in mammals, including humans, is catalyzed by UDP-glucose pyrophosphorylase. Recognizing the difference between the critical use of UDPGlc PPase in mammals as compared to the use of ADPGlc PPase in certain pathogenic bacteria, the present inventor first recognized that such bacteria could be selectively killed by inhibiting the activity of ADPGlc PPase, without adversely affecting any mammal so infected with the bacteria. This selectivity provides a basis and target for a novel and important new class of antibiotics, antibiotics which are inhibitors of energy storage and utilization enzymes, namely ADPGlc PPase inhibitors.

Step (2) in the above is catalyzed in humans by glycogen synthase (EC 2.4.1.11), whereas in many pathogenic bacteria the corresponding enzyme is EC 2.4.1.21 because the sugar substrate is ADP-based, not UDP-based. Again, this provides a target for a novel and important new class of antibiotics which inhibit glycogen synthase (EC 2.4.1.21).

As is well known, antibiotics are currently used to treat a wide range of bacterial infections, ranging from minor to life threatening infections. Broad spectrum antibiotics treat a variety of gram-positive and gram-negative organisms, while mild spectrum antibiotics only cover limited types of bacterial organisms and are useful for curing infections with known bacterial strains.

But it has recently been noted that pathogenic bacteria and fungi increasingly exhibit resistance to existing classes of antibiotics, such as penicillin, vancomycin and erythromycin. According to the Center for Disease Control, pathogenic resistance has significantly increased mortality rates, making infectious disease the third largest cause of death in the United States. The rates of antibiotic resistant bacteria have particularly increased recently with respect to *S. aureus*, Enterococcus strains, *S. pneumoniae* and *M. tuberculosis*.

The mechanism of action for most antibiotics is the inhibition of bacterial cell wall completion, or DNA or protein synthesis. Sulfonamides and trimethoprin act by inhibiting an essential metabolic step, namely folate synthesis. But there is a great need for new antibiotics with different targets, especially in light of the ever increasing problem of resistant strains.

The present inventor has found that compounds which act as inhibitors of ADP-glucose pyrophosphorylase and/or glycogen synthase offer another class of antibiotics which inhibit an essential bacterial metabolic step, namely a pathway essential for bacterial energy storage and utilization. A fist aspect of the invention relates to a method for identifying compounds capable of inhibiting the growth of pathogenic microorganisms which comprises:
 a. identifying an enzyme that is important to energy storage or utilization in the pathogenic microorganism, which enzyme is not present in mammals, particularly not in humans; and
 b. identifying a compound that inhibits that enzyme in the pathogenic microorganism.

According to the present invention, an enzyme in an energy storage or utilization pathway which is important to continued growth and viability of a pathogenic microorganism but which is absent in humans provides a unique, specific target for compounds which can inhibit infections of such pathogenic microorganisms without causing undesirable side effects or toxicity to a mammalian patient. Various biosynthetic pathways have been identified in the literature for various microorganisms and for mammals, and those pathways, which include an important enzyme present in pathogenic microorganisms but absent in mammals, provide a unique target for screening for compounds useful for inhibiting pathogenic microorganism infections.

According to the present invention, the present inventor has specifically identified ADP-glucose pyrophosphorylase (EC 2.7.7.27) and glycogen synthase (EC 2.4.1.21) as enzymes present in a biosynthetic pathway important for energy storage and utilization in pathogenic microorganisms, but absent in mammals, specifically absent in humans. Since the biosynthetic pathway is important for energy storage or utilization in pathogenic microorganisms, inhibition of this pathway significantly decreases the viability of pathogenic microorganisms, leading ultimately to death of the microorganism, either by action of the inhibitor alone, or in combination with the patient's own immunological systems for resisting infections, or in combination with other antibiotics.

In some instances, inhibition of the biosynthetic pathways and/or inhibition of ADP-glucose pyrophosphorylase (EC 2.7.7.27) or glycogen synthase (EC 2.4.1.21) may not per se kill the bacteria, but will render the microorganisms non-infective or non-pathogenic. It has been known for quite some time that complex carbohydrates can act as virulence factors in bacteria responsible for invasive infections (Glazer, A. N. and Nikaido, H. Microbial Biotechnology. Fundamentals of Applied Microbiology (1995) W. H. Freeman and Co., pgs. 266–272). Specific to glycogen biosynthesis, Uttaro, A. D., and Ugalde, R. A. Gene 150: 117–122 (1 994) and J. E. Ugalde et al. J. Bact. 180: 6557–64 (1998) have shown that mutations that prevent gene expression of the g/g operon render *Agrobacterium tumefaciens* non-infective. Illiffe-Lee and McClarty, Mol. Microbiology 38(1): 20–30 (2000) have shown that growth of *Chlamydia trachomatis*, under conditions that limit glycogen, severely reduces the number of infectious bodies.

Although not considered a limiting list, the present inventor has specifically identified a number of important pathogenic microorganisms which require ADP-glucose pyrophosphorylase (EC 2.7.7.27) and glycogen synthase (EC 2.4.1.21), including *Chlamydia pneumoniae, Chlamydia trachomatis, Esherichia coli* O157, *Haemophilus influenzae, Mycobacterium leprae, Mycobacterium tuberculosis, Salmonella tphimurium* and *Vibrio cholerae, Streptococcus pneumoniae, Yersinia pestis, Bacillus subtilus* and *Bacillus anthracis*.

The above listed bacteria comprise some of the most important pathogenic microorganisms which account for significant numbers of disease patients in the United States and around the world. The following table summarizes the prevalence and current treatments available for these pathogenic microorganisms.

TABLE 1

Prevalence and Current Treatments

| Microorganism | Disease(s) | Incidence (estimated number of new cases/yr) | Prevalence (estimated number of people currently infected) | Treatment |
|---|---|---|---|---|
| *Chlamydia pneumoniae* | Acute and chronic respiratory diseases including: pneumonia, pharyngitis, bronchitis, sinusitis, otitis media, COPD, asthma, Reiter syndrome, and sarciodosis. | | | |
| *Chlamydia trachomatis* | STD and blindness (trachoma). | 3 million/yr STD | 89 million/yr STD; 400 million partially blind, 6 million totally blind. | Doxcycline, tetracycline, chloramphenicol, refampicin, fluroquinones, erythromycin, and azithromycin |
| *Escherichia coli* O157 (food poisoning) | Abdominal cramps, non-bloody diarrhea, hemorrhagic colitis, and haemolytic-uraemic syndrome. | | | |
| *Haemophilus influenzae* | Bacteremia, acute bacterial meningitis, otitis media, sinusitis, and pneumonia. | 3.5 million/yr | | Ampicillin, cephalosporin, chloramphenicol, tetracycline, sulfa drugs, and amoxicillin |
| *Mycobacterium leprae* | Leprosy (Hansen's disease) | 250 new cases/yr in the U.S., 600,000 new cases/yr world-wide. | 12 million world-wide. It is a public health problem in 72 countries, 19 of which account for 90% of all the cases in the world. | Dapsone, refampin, ethionamide |
| *Mycobacterium tuberculosis* | Tuberculosis | >20,000 in the U.S. | 16 million world-wide. According to the WHO, tuberculosis is the number one killer among infectious diseases in the world. TB kills more people than AIDS, malaria, and tropical diseases combined. | Isoniazid, rifampin, ethambutol, and pyrazinamide. |
| *Salmonella typhimurium* | Salmonellosis, abdominal cramps, non-bloody diarrhea. | >50,000/yr world-wide | | Ampicillin, chloramphenicol, streptomycin. sulphonamides, and tetracycline |
| *Vibrio cholerae* | Cholera | >50,000/yr; mostly in southeast asia. | Over 1,000,000 reported cases throughout the world. Usually epidemic or pandemic. | |

Description of Method for Inhibition Screening

As noted above, one aspect of the present invention is a method for the identification of a compound capable of inhibiting the growth of pathogenic microorganisms by interfering with the activity of glycogen synthase and/or ADP-glucose pyrophosphorylase. Compounds can be identified by growing bacteria on defined media in the presence or absence of a test compound, and assessing the effect on glycogen synthesis by iodine staining of colonies (Govons, S. et al (1969) *J. Bacteriol.* 97, 970–972). More quantitatively, the amount of glucan accumulated in the absence or presence of test compounds can be assessed by collection of the glycogen from the culture and quantitatively converting it to glucose with glucoamylase and α-amylase (Preiss, J. et al (1975) *J. Biol. Chem.* 250: 7631–7638) Compounds capable of inhibiting glycogen synthase and/or ADP-glucose pyrophorylase can also be identified by means of in vitro experiments by exposing a substrate comprising glycogen synthase and/or ADP-glucose pyrophosphorylase to a plurality of test compounds and identifying those compounds which inhibit the tested enzyme according to known catalytic measurement techniques.

One particular in vitro method for assessing the activity of an inhibitor to purified ADPGlc PPase is the following:

Assaying for ADPGlc synthesis activity involves measuring the amount of 14-C labeled Glc-1-P converted to ADPGlucose (Preiss, J., Shen, L., Greenberg, E., and Gentner, N. (1966) *Biochemistry* 5, 1833–1845). Briefly, unreacted Glc-1-P is separated from product by the following steps: 1) digestion with alkaline phosphatase (thus removing the negatively charged phosphate); 2) spotting an aliquot of the reaction mixture on to positively charged DE-81 filters (Whatman); and 3) washing the filters with water (thus removing the now neutral C-14 glucose).

To assess the effect of a putative inhibitor, enzyme assays are performed at a subsaturating concentration of substrate (depending on the enzyme, ATP=0.2–1 mM, Glc-1-P=0.5 mM) under standard conditions in the absence and presence of the major activator for each enzyme (1–5 mM depending on enzyme). In this way, the effect of the inhibitors can be evaluated under the range of the expected in vivo conditions. Initial screening of a putative inhibitor typically includes testing at two concentrations (~25 $\mu$M and 1 mM)±major activator with appropriate controls and blanks for a total of 9 assays/inhibitor/enzyme (2 control assays—appropriate enzyme concentrations in the absence of inhibitor; 4 experimental assays; 1 blank in the absence of inhibitors; 2 blanks in the presence of inhibitor (no activator required).

A quantitative assay to measure the activity of an inhibitor to bacterial (ADPG dependent) Glycogen Synthase (EC 2.4.1.21) involves the measurement of incorporated 14-C-labeled ADPGlc into a glucan molecule (a specific glycogen, or amylopectin) that serves as a primer wherein the labeled glucan can easily be separated from unincorporated ADPGlc by a precipitation step (methanol insoluble polysaccaride). Useful specific procedures are as described in Furakawa, K., Tagaya, M., Inouye, M., Preiss, J., and Fukui, T. (1990) "Identification of Lys-15 at the Active Site in *E.coli* Glycogen Synthase," J. Biol. Chem. 265, 2086–2090; and Thomas, J. A., Schlender, K. K., and Larner, J. (1968) Anal. Biochem. 25, 486–499.

Useful inhibitors can also be identified, and potential inhibitors assessed, by in vitro treatment of bacteria in, for example, culture tubes or petri dish samples. Such assessments can be performed, for example, by spreading a measured aliquot of a diluted bacterial culture into nutrient agar plates, both treated and control, and counting the number of visible cells. Detailed procedures are well known to those in the art, as shown for example in Miller, *Experiments in Molecular Genetics,* Cold Spring Harbor Laboratory, 1972.

Compounds which inhibit ADPGlc PPase or glycogen synthase can also be assessed in an in vivo animal model test. Such tests can be conducted in an animal which is susceptible to infection by the pathogenic microorganism of interest. For example, the effect of the test compound on the virulence of *H. influenzae* is assessed by comparing the survival rates of animals which have been administered the test compound with the survival rate of animals which have not been administered the test compound, wherein a higher survival rate of animals administered the test compound is an indication that the test compound has an effect on the virulence of *H. influenzae.*

To determine the effect of a test compound on colonization of the mucosal surface or on invasiveness and/or virulence of *H. influenzae,* the test compound is administered to the animals either prior to, at the time of, or after inoculation of the animals with *H. influenzae.* The test compound may be administered directly into the nasopharynx, or may be administered by any other route including any one of the traditional modes (e.g., orally, parenterally, transdermally or transmucosally), in a sustained release formulation using a biodegradable biopolymer, or by on-site delivery using micelles, gels and liposomes, or rectally (e.g., by suppository or enema). Precise formulations and dosages will depend on the nature of the test compound and may be determined using standard techniques, by a pharmacologist of ordinary skill in the art.

There are essentially two types of in vivo models in which a compound may be tested for antibiotic activity directed against *S. pneumoniae.* In the first model, colonization of the mucosal surface of the nasopharynx by *S. pneumoniae* in the presence or absence of the test compound is assessed. Measurement of colonization of the mucosal surface of the nasopharynx by *S. pneumoniae* may be conducted in an animal model essentially as described in Weiser et al. (1994, supra).

To assess colonization, briefly, an amount of *S. pneumoniae,* generally about 10 mu.l of phosphate buffered saline (PBS)-washed mid log phase organisms adjusted to the desired density, is inoculated into the left anterior naris of the animal. Colony counts are performed to ensure that the inocula are of the desired density and phenotype. The nasopharynx is cultured for the presence of viable *S. pneumoniae* by the slow instillation of 20 to 40 $\mu$l of sterile PBS into the left naris and withdrawal of the initial 10 $\mu$l from the right naris. This procedure ensures that the fluid has passed through the nasopharynx. The quantity of organisms recovered is then assessed in a well known culture assay.

The effect of the test compound on colonization of the nasopharynx by *S. pneumoniae* is evaluated by comparing the degree of colonization of the nasopharynx in animals which have been administered the test compound with the degree of colonization in animals which have not been administered the test compound, wherein a lower degree of colonization in animals administered the test compound is an indication that the test compound inhibits colonization of the nasopharynx by *S. pneumoniae.*

The invasive capability of *S. pneumoniae* may also be measured in the same animal model. Essentially, bacteria which have entered the blood stream following inoculation of the nasopharynx are detected by culturing the same in a sample of blood obtained from the animal. Again, the effect of the test compound on the invasive capacity of *S. pneumoniae* is assessed by comparing the number of organisms found in the blood stream in animals which have been administered the test compound with the number of organisms in the blood stream in animals which have not been administered the test compound, wherein a lower number of organisms in the blood stream of animals administered the test compound is an indication that the test compound has an effect on the invasive capacity of *S. pneumoniae.*

In a second in vivo model, the virulence of *S. pneumoniae* is assessed in animals as described in Berry et al. (1995, Infect. Immun. 63:1969–1974). Essentially, cultures of *S. pneumoniae* are diluted to a density of 2.times.10.sup.6 colony forming units per ml, and volumes of 0.1 ml are injected intraperitoneally into groups of animals. The survival time of the animals is recorded and the differences in median survival time between groups may be analyzed by the Mann-Whitney U test (two-tailed). Differences in the overall survival rate between groups may be analyzed by the x.sup.2 test (two tailed).

The effect of the test compound on the virulence of *S. pneumoniae* is assessed by comparing the survival rates of animals which have been administered the test compound with the survival rate of animals which have not been administered the test compound, wherein a higher survival rate of animals administered the test compound is an indication that the test compound has an effect on the virulence of *S. pneumoniae.*

To determine the effect of a test compound on colonization of the mucosal surface or on invasiveness and/or virulence of *S. pneumoniae,* the test compound is administered to the animals either prior to, at the time of, or after inoculation of the animals with *S. pneumoniae.* The test compound may be administered directly into the nasopharynx, or may be administered by any other route including any one of the traditional modes (e.g., orally, parenterally, transdermally or transmucosally), in a sustained release formulation using a biodegradable biopolymer, or by on-site delivery using micelles, gels and liposomes, or rectally (e.g., by suppository or enema). Precise formulations and dosages will depend on the nature of the test compound and may be determined using standard techniques, by a pharmacologist of ordinary skill in the art.

The present invention further provides a method for treating pathogenic microorganism infections in a patient by administering to the patient an effective amount of an inhibitor against glycogen synthase and/or ADP-glucose pyrophosphorylase, wherein an effective amount of the inhibitor will inhibit the activity of the enzyme so as to decrease viability of and/or kill the microorganism. The inhibitor utilized in the treatment may be one identified by one of the methods described above, or inhibitors may be identified by any other method. One such inhibitor is the nucleoside α-P-boranodiphosphoglucose (particularly its triethylammonium salt), which is a borane analog of glucose-conjugated nucleoside diphosphate, described by Lin and Shaw, *Tetrahedron Letters* 41 (2000) 6701–6704. The particular compound, adenosine α-P-boranodiphosphoglucose, is a boran analog of ADP-glucose generating two sterioisomers and has the following structures:

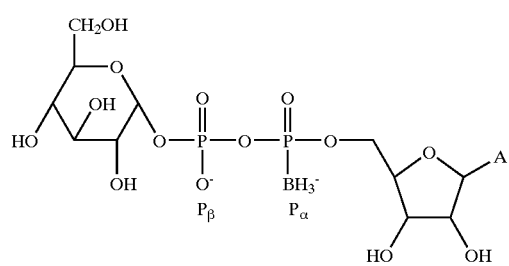

(I)

wherein A is adenosine.

Adenosine boranophosphate exists as two stereoisomers, the preparation of which is described below:

Scheme 1
Synthesis of adenosine boranophosphonate

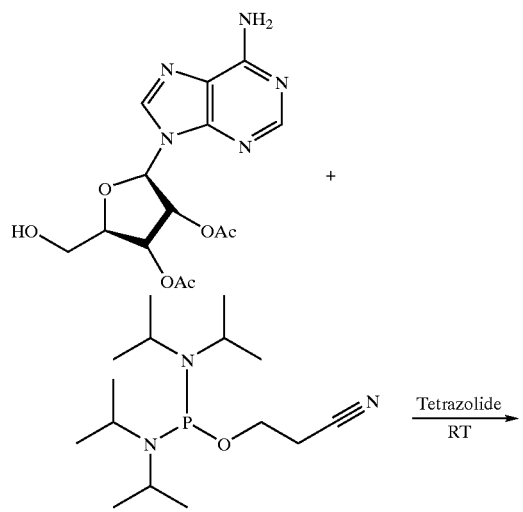

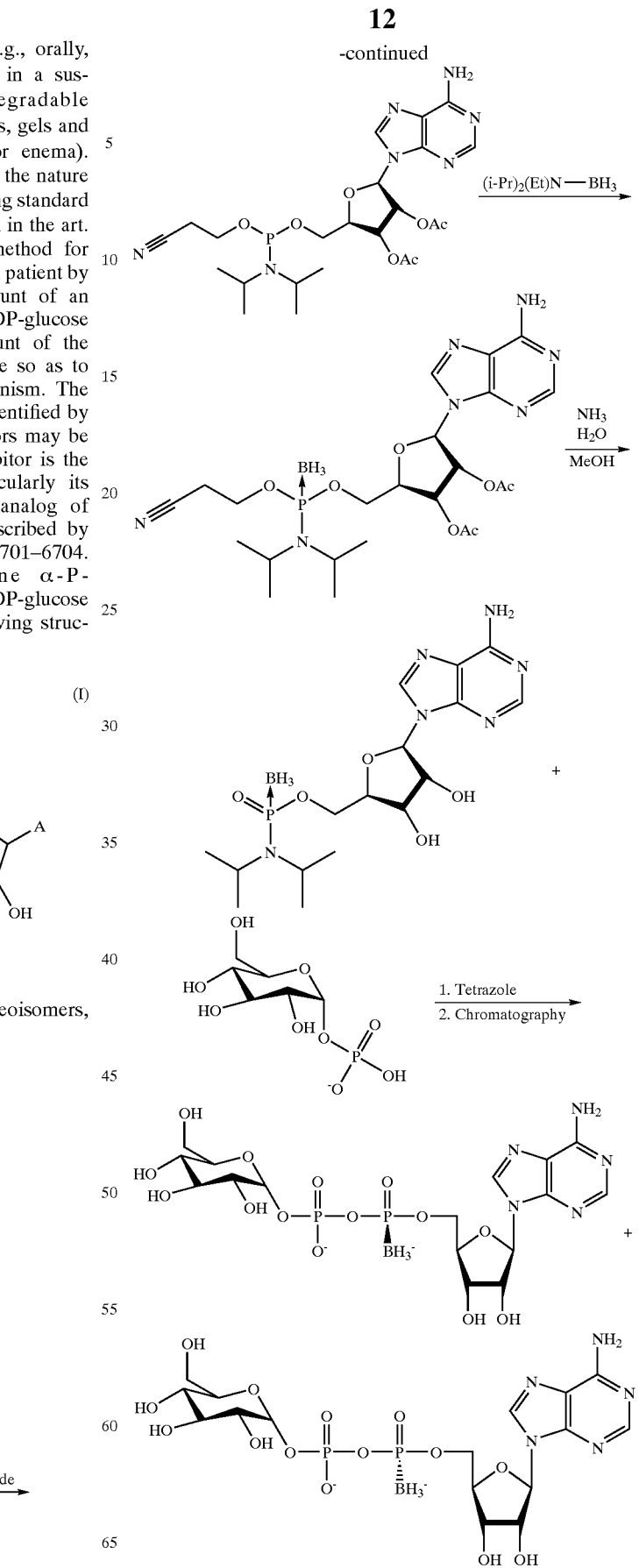

As an analog of ADP-glucose, the compound of formula (I) is a useful inhibitor of ADPGlc PPase according to the present invention. Other known regulators and inhibitors of ADPGlc PPase are the following:

TABLE 2

Regulatory properties of ADP-glucose pyrophosphorylase in different organisms

| Organism | ADP-glucose pyrophosphorylase | |
|---|---|---|
| | Allosteric regulators Activator | Inhibitor |
| Prokaryotes | | |
| Enterobacteria | | |
| *Escherichia coli* | Fructose-1,6-bisP | AMP |
| *Salmonella typhimurium* | | |
| *Enterobacter aerogenes* | | |
| *Aeromonas formicans* | Fructose-1,6-bisP | AMP |
| *Micrococcus luteus* | Fructose-6-P | ADP |
| *Mycobacterium smegmatis* | | |
| *Serratia mercescens* | None | AMP |
| *Enterobacter hafniae* | | |
| *Clostridium pasteurianum* | | |
| *Agrobacterium tumefaciens* | Pyruvate | AMP |
| *Arthrobacter viscosus* | Fructose-6-P | ADP |
| *Chromatium vinosum* | | |
| *Rhodobacter capsulata* | | |
| *Rhodomicrobium vannielii* | | |
| *Rhodobacter gelatinosa* | Pyruvate | AMP |
| *Rhodobacter globiformis* | Fructose-6-P | Pi (inorganic phosphate) |
| *Rhodobacter sphaeroides* | Fructose-1,6-bisP | |
| *Rhodospirillum rubrum* | Pyruvate | |
| *Rhodospirillum tenue* | | |
| *Rhodocyclus purpureus* | | |
| Cyanobacteria | 3-P-glycerate | Pi |
| Synechococcus 6301 | | |
| Synechocysits 6803 | | |
| Anabaena 7120 | | |
| Eukaryotes | 3-P-glycerate | Pi |
| Green algae | | |
| *Chlorella fusca* | | |
| *Chlorella vulgaris* | | |
| *Chlamydomonas reinhardtii* | | |
| Higher Plants | | |
| Photosynthetic tissues (leaves of spinach, Arabidopsis, wheat, maize, rice) | 3-P-glycerate | Pi |
| Non-photosynthetic tissues (Potato tubers, maize endosperm) | 3-P-glycerate | Pi |

EXAMPLE 1

Effect of ADPG Borano Analogs on Rhodobacter Sphaeroides (RB.S.) ADPG PPASE

The APDGlc Ppase from *Rhodobacter sphaeroides* has been used as a model enzyme for initial testing of inhibitors as it has been cloned, sequenced, and expressed in the inventor's laboratory (Meyer et al (1999) *Arch. Biochem. Biophys.* 372, 179–188; Igarashi, R. Y. and Meyer, C. R. (2000) *Arch. Biochem. Biophys.* 376, 47–58) and the purified recombinant enzyme is readily available. Further, this particular enzyme has the most complex regulation (having partial overlap with nearly every type of ADPG Ppase) and has sufficient homology (ranging from ~40–70% similarity) to the enzyme primary sequence from the mentioned pathogenic bacteria.

1. OVERVIEW:

2 analogs (ANALOG; stereoisomers I, II) of adenosine-α-P-boranodiphosphoglucose were tested for inhibiting activity against the ADPG Ppase enzyme from Rhodobacter sphaeroides (Rb.s.) ADPG Ppase.

2. MATERIALS

PREMIX: A: 100 mM HEPES (pH 7), 0.5 mg/mL BSA, 0.5 mM Glc-1-P, 0.25 mM ATP subsaturating (near S0.5 value), 5 mM MgCl2, (0.2 U Pyrophosphatase))

PREMIX B: A+1 mM F6P (170 µL premix will allow 20 µL for analog vol., 10 µL of E)

II. ANALOG CONC.=5, 50, 500 µM (STOCK CONC.=5 mM) in 50 mM HEPES, pH 7, note that 20 µL of 5 mM in 200 µL assay will yield 500 µM final concentration to obtain 5 mM aliquots:

ANALOG I: add 625 µL of HEPES buffer, mix thoroughly

ANALOG II: add 500 µL of HEPES buffer, mix thoroughly

1:10 DILUTION ALIQUOTS OF 5 mM STOCKS are prepared in order to generate stock solutions that will give 50 and 5 µM with the addition of 20 µL. 100 µL aliquots are stored at −20 C RBS ADPG PPASE WT ENZYME CONC.=17 mg/mL (use 1:8000 dilution in Dilution Buffer)

THE FOLLOWING ASSAY SET OF 11 ARE UTILIZED FOR EACH ANALOG

1-BLANK (Premix A)

2-BLANK+50 µM ANALOG (A)

3-BLANK+500 µM ANALOG (A)

4-E CON (A)

5-E CON+F6P (B)

6-E+5 µM (A)

7-E+5 µM((B)

8-E+50 µM(A)

9-E+50 µM(B)

10-E+500 µM (A)

11-E+500 µM (B)

Purified Rb.s ADPG Ppase was assayed under standard conditions (0.25 mM ATP [~S0.5 value], 0.5 mM Glc-1-P, 5 mM Mg, 100 mM HEPES, pH7) in the presence and absence of the activator F6P (1 mM) at 3 concentrations of the analogs: 5, 50, and 500 µM. Analog stock solutions were made in 50 mM HEPES, pH 7). These concentrations should be regarded as estimates as there could have been some breakdown of the compounds during 2 years of storage at −20° C. The analogs had no effect on the background cpm of the assays.

Results

Figure 2:
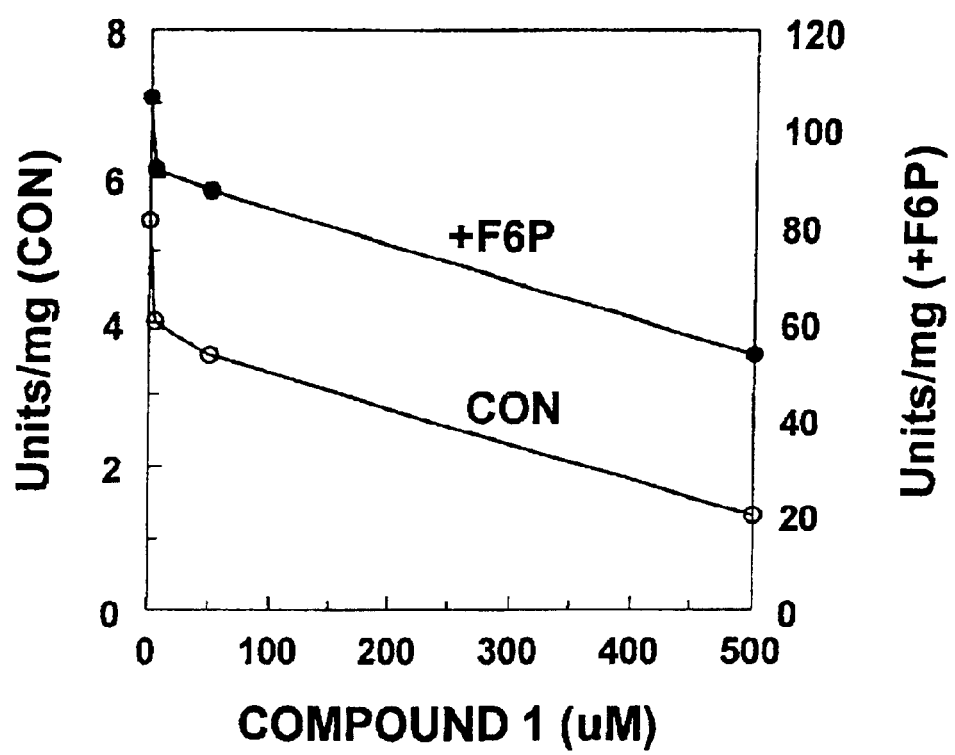
Figure 3:
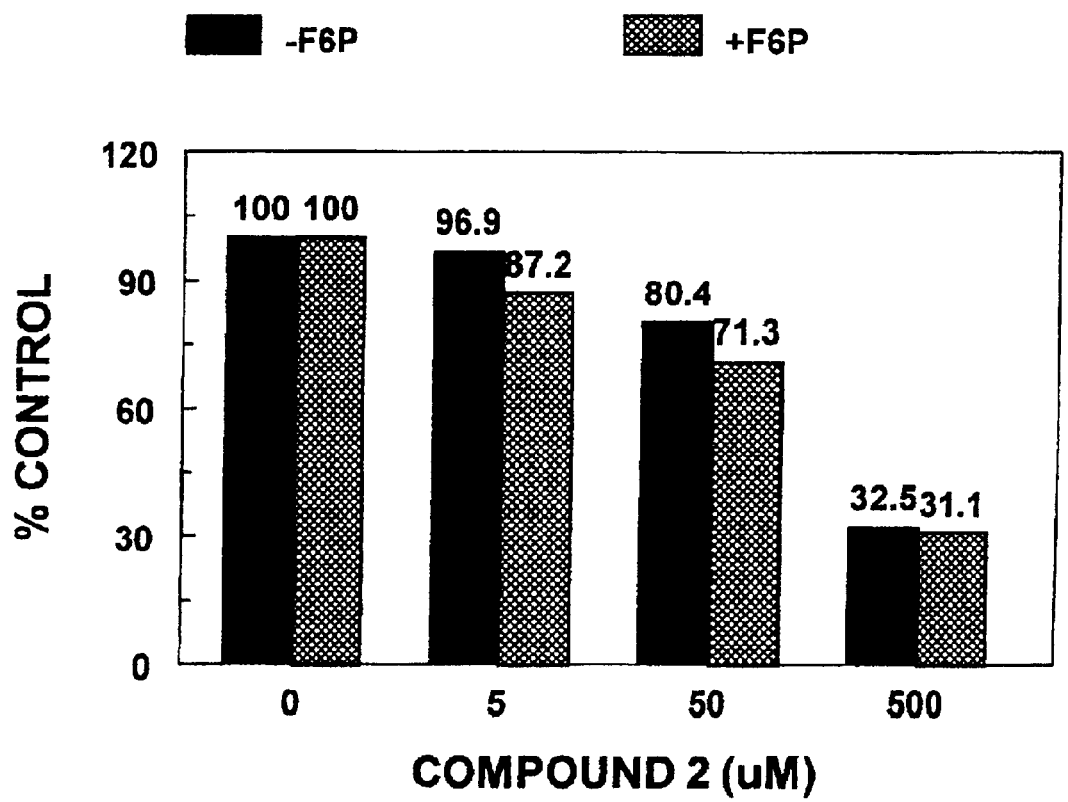
Figure 4:
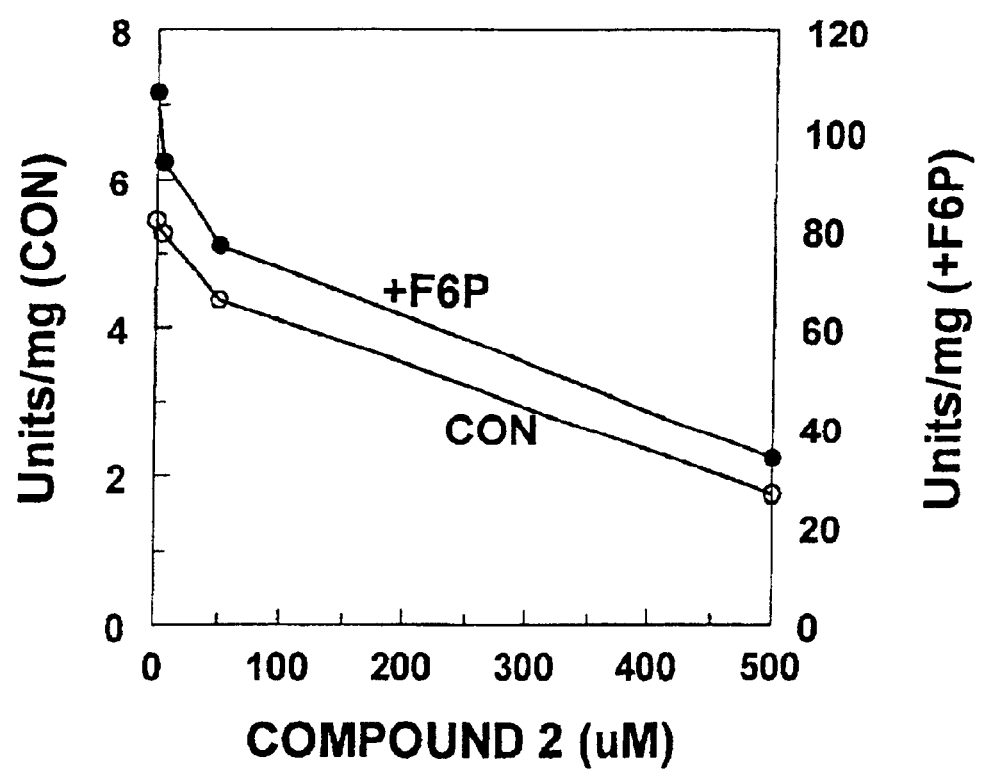
Figure 5:
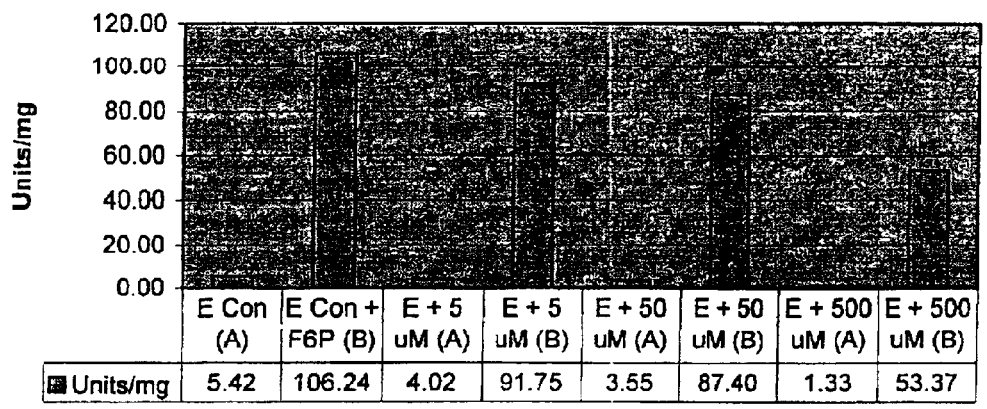
Figure 5:
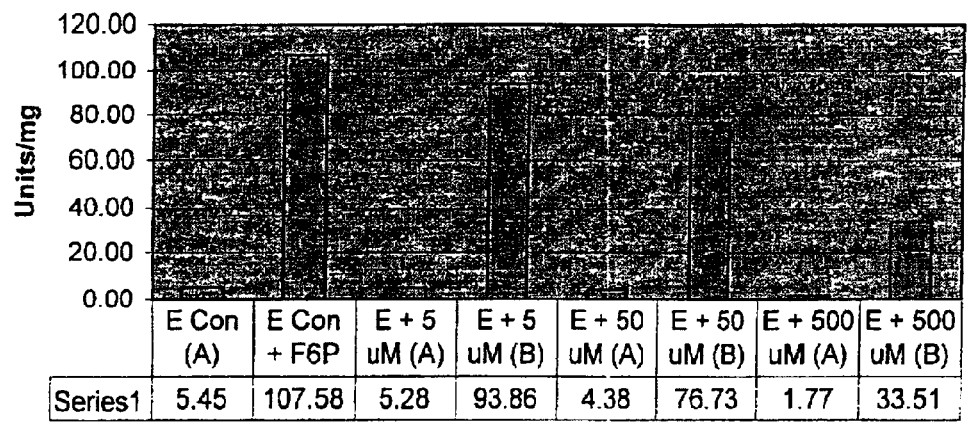

The detailed experimental data results are set forth in Table 3, and those results are graphed in FIGS. 1–5.

Analog I successfully inhibited the Rb.s. ADPG Ppase. While the response may be biphasic, the results showed about 75% inhibition by 500 µM in the absence of the activator F6P. The inhibition was less in the presence of F6P (~50% at 500 µM). Analog II also successfully inhibited the Rb.s. enzyme with about 70% inhibition at 500 µM in both the presence and absence of F6P.

TABLE 3

Inhibition Study with ADFGlucose Borano compounds Analog I and II

|  | Analog I | Analog II |
|---|---|---|
| Blank | 60.33 | 56.33 |
| Blank + 50 Um | 76.33 | 51.00 |
| Blank + 500 uM | 53.67 | 53.33 |

825 Cpm/nmol

| Description | Dil | Volume (uL) | CPM | cor. CPM | nmol | *2.2 | nmol/min | nmol/min/uL | dil. Corr nmol/min/uL | Units/mg |
|---|---|---|---|---|---|---|---|---|---|---|
| E Con (A) | 8000 | 10 | 492.00 | 431.67 | 0.52 | 1.151 | 0.115 | 0.0115 | 92.090 | 5.42 |
| E Con + F6P (B) | 8000 | 10 | 8526.00 | 8465.67 | 10.26 | 22.575 | 2.258 | 0.2258 | 1806.010 | 106.24 |
| E + 5 uM (A) | 8000 | 10 | 380.67 | 320.34 | 0.39 | 0.854 | 0.085 | 0.0085 | 68.339 | 4.02 |
| E + 5 uM (B) | 8000 | 10 | 7371.33 | 7311.00 | 8.86 | 19.496 | 1.950 | 0.1950 | 1559.680 | 91.75 |
| E + 50 uM (A) | 8000 | 10 | 359.33 | 283.00 | 0.34 | 0.755 | 0.075 | 0.0075 | 60.373 | 3.55 |
| E + 50 uM (B) | 8000 | 10 | 7041.00 | 6964.67 | 8.44 | 18.572 | 1.857 | 0.1857 | 1485.796 | 87.40 |
| E + 500 uM (A) | 8000 | 10 | 160.00 | 106.33 | 0.13 | 0.284 | 0.028 | 0.0028 | 22.684 | 1.33 |
| E + 500 uM (B) | 8000 | 10 | 4306.67 | 4253.00 | 5.16 | 11.341 | 1.134 | 0.1134 | 907.307 | 53.37 |
| E Con (A) | 8000 | 10 | 491.00 | 434.67 | 0.53 | 1.159 | 0.116 | 0.0116 | 92.730 | 5.45 |
| E Con + F6P (B) | 8000 | 10 | 8629.00 | 8572.67 | 10.39 | 22.860 | 2.286 | 0.2286 | 1828.836 | 107.58 |
| E + 5 uM (A) | 8000 | 10 | 477.00 | 420.67 | 0.51 | 1.122 | 0.112 | 0.0112 | 89.743 | 5.28 |
| E + uM (B) | 8000 | 10 | 7536.00 | 7479.67 | 9.07 | 19.946 | 1.995 | 0.1995 | 1595.663 | 93.86 |
| E + 50 uM (A) | 8000 | 10 | 399.67 | 348.67 | 0.42 | 0.930 | 0.093 | 0.0093 | 74.383 | 4.38 |
| E + 50 uM (B) | 8000 | 10 | 6165.33 | 6114.33 | 7.41 | 16.305 | 1.630 | 0.1630 | 1304.390 | 76.73 |
| E + 500 uM (A) | 8000 | 10 | 194.33 | 141.00 | 0.17 | 0.376 | 0.038 | 0.0038 | 30.080 | 1.77 |
| E + 500 uM (B) | 8000 | 10 | 2724.00 | 2670.67 | 3.24 | 7.122 | 0.712 | 0.0712 | 569.743 | 33.51 |

Inhibitors useful for the treatment of pathogenic bacteria and microorganisms can be administered by a variety of means and dosage forms well known to those skilled in the art. When used as an antimicrobial agent in the treatment of microorganism infections, the present compounds are administered, for example, orally in the form of a tablet, capsule, powder, syrup, etc., or parenterally such as intravenous injection, intramuscular injection, or intrarectal administration.

The suitable administration forms as mentioned above may be prepared by mixing an active ingredient with a conventional pharmaceutically acceptable carrier, excipient, binder, stabilizer, etc. When administered in the form of an injection, a pharmaceutically acceptable buffering agent, solubilizer, isotonic agent, etc. may be added thereto. The active compound may be administered per se, or in the form of a pharmaceutically acceptable salt thereof, or in the form of a pro-drug, such as an ester.

The dosage of the compound varies according to the conditions, ages, weights of the patient, the administration form, the frequency of the administration, etc., but it is usually in the range of 100 to 3000 mg per day for an adult, which is administered once or divided into several dosage units.

All of the publications referred to herein, are hereby specifically incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A method of identifying a compound capable of inhibiting the growth of a pathogenic microorganisms which comprises:
   (a) identifying an enzyme involved in the conversion of α-glucose-1-phosphate+ATP into ADP-glucose+Ppi, which enzyme is present in a pathogenic microorganism but is not present in humans;
   (b) identifying a compound that inhibits the conversion of α-glucose-1-phosphate+ATP into ADP-glucose+Ppi by binding to said enzyme; and
   (c) exposing said pathogenic microorganism to said compound to determine the effect of said compound on the growth of said pathogenic microorganism.

2. The method according to claim 1, wherein said enzyme is ADP glucose pyrophosphorylase (EC 2.7.7.27).

3. A method of identifying a compound capable of inhibiting the growth of a pathogenic microorganism by interfering with the activity of ADP-glucose pyrophosphorylase (EC 2.7.7.27) by binding to said ADP glucose pyrophosphorylase which method comprises:
   (a) identifying an enzyme involved in the conversion of α-glucose-1-phosphate+ATP into ADP-glucose+Ppi, which enzyme is present in a pathogenic microorganism but is not present in humans;
   (b) identifying a compound that inhibits the conversion of α-glucose-1-phosphate+ATP into ADP-glucose+Ppi by binding to said enzyme; and
   (c) incubating a sample of said pathogenic microorganism in a media in the presence or absence of said compound, and assessing the effect on conversion of α-glucose1-phosphate, wherein a lower level of conversion of α-glucose-1-phosphate in the presence of said compound, compared with the level of conversion of α-glucose-1-phosphate in the absence of said compound, indicates that said test compound interferes with the activity of ADP glucose pyrophosphorylase (EC 2.7.7.27) by binding to said ADP glucose pyrophosphorylase.

4. A method of identifying a compound capable of inhibiting the growth of a pathogenic microorganism by interfering with the activity of ADP glucose pyrophosphorylase (EC 2.7.7.27) which method comprises:
   (a) identifying an enzyme involved in the conversion of α-glucose-1-phosphate+ATP into ADP-glucose+Ppi, which enzyme is present in a pathogenic microorganism but is not present in humans;
   b) exposing a substrate comprising ADP glucose pyrophosphorylase (EC 2.7.7.27) to a plurality of test compounds and identifying an active test compound which binds to said ADP glucose pyrophosphorylase (EC 2.7.7.27); and (c) exposing said pathogenic microorganism to said compound to determine the effect of said compound on the growth of said pathogenic microorganism.

5. The method of claim 4, wherein said substrate comprises a plurality of ADP glucose phosphorylase (EC 2.7.7.27) molecules and said test compounds comprise a label to permit identification of a test compound which binds to ADP glucose pyrophosphorylase (EC 2.7.7.27).

6. The method according to any one of claims 1, 2, 3, 4, and 5, wherein said pathogenic microorganism is a member selected from the group consisting of *Chlamydia pneumoniae, Chlamydia trachomatis, Esherichia coli* O157, *Haemophilus influenzae, Mycobacterium leprae, Mycobacterium tuberculosis, Salmonella typhimurium* and *Vibrio cholerae, Streptococcus pneumoniae, Yersinia pestis, Bacillus subtilus* and *Bacillus anthracts*.

7. The method according to any one of claims 2, 3, 4, and 5, wherein said ADP glucose pyrophosphorylase (EC 2.7.7.27) is in the form of a purified enzyme product.

* * * * *